United States Patent [19]

Dokter et al.

[11] 4,376,264
[45] Mar. 8, 1983

[54] METHOD OF CHECKING THE AUTHENTICITY OF PAPERS AND PHYSICALLY IDENTIFIABLE PAPER FOR USE IN SAID METHOD

[75] Inventors: Hendrik D. Dokter, Ugchelen; Roelof Hildering, Frederikslaan; Adrianus Mackor, Hollandsche Rading, all of Netherlands

[73] Assignee: Papierfabrieken Van Houtem & Palm B.V., Ugchelen, Netherlands

[21] Appl. No.: 231,178

[22] Filed: Feb. 4, 1981

[30] Foreign Application Priority Data

Feb. 6, 1980 [NL] Netherlands ......................... 8000734

[51] Int. Cl.³ ............................................ G01N 27/00
[52] U.S. Cl. .................................... 324/316; 324/300
[58] Field of Search ............... 324/300, 317, 307, 316; 356/71, 73

[56] References Cited

U.S. PATENT DOCUMENTS

| | | | |
|---|---|---|---|
| 2,951,164 | 8/1960 | Timms | 356/73 |
| 3,348,136 | 10/1967 | Nelson et al. | 324/317 |
| 3,358,222 | 12/1967 | Hyde | 324/300 |
| 3,480,785 | 11/1969 | Aufderheide | 356/71 |
| 3,491,243 | 1/1970 | Tsugami | 356/71 |
| 4,267,620 | 5/1981 | Allen, Jr. | 324/300 |

Primary Examiner—Michael J. Tokar
Attorney, Agent, or Firm—Browdy & Neimark

[57] ABSTRACT

A method of checking the authenticity of papers, such as banknotes, is provided which comprises using authentic paper containing a minor amount of substance showing an ESR spectrum at room temperature and checking the authenticity by ESR spectroscopy, as well as paper for use in said method, containing a minor amount of a compound showing an ESR spectrum at room temperature, said compound being either an oxide or salt having a crystal lattice of cubic symmetry doped with such a metal, or an oxide or salt of arbitrary symmetry doped with a freely rotatable ion containing such a metal.

10 Claims, 6 Drawing Figures

METHOD OF CHECKING THE AUTHENTICITY OF PAPERS AND PHYSICALLY IDENTIFIABLE PAPER FOR USE IN SAID METHOD

This invention relates to a method of checking the authenticity of papers, more specifically of banknotes, cheques and the like, in a physical way, as well as to physically identifiable paper for use in this method.

Various methods have been proposed for identifying valuable papers. Thus, it has been proposed in Dutch patent application No. 6613250 to incorporate in paper or the like a drying catalyst for inks based on oil or oil derivatives According to page 5, lines 10 a.f. of this Dutch application it is possible to choose catalysts which also have the advantage that they can be detected in a chemical way with the aid of spot reactions. Cobalt acetate and manganous sulfate are mentioned as such compounds. These compounds happen to be compounds of metals having a not completely filled 3d orbital so that in principle they could also be detected in a physical way suitable therefor, for instance with the aid of electron spin resonance spectroscopy (hereinafter electron spin resonance will usually be abbreviated in the usual way as "ESR"). The so obtained paper is intended in the first place for the production of banknotes, cheques and the like.

Identification of various papers with the aid of fluorescence has also been proposed, vide French Pat. Nos. 2,289,976; U.S. Pat. No. 4,146,792 and DE-OS No. 2,745,301. According to these publications a compound capable of fluorescence and containing one or more rare earth elements is incorporated in the paper, data card or the like, and the authenticity of the document is checked by means of a fluorescence device.

Although fluorescence per se is a suitable physical means of detecting forgery, it should be taken into account that forgery is inclined to get more and more sophisticated so that also more and more sophisticated methods are necessary in order to protect the public against this kind of crime. Especially in the case of forgery of banknotes it is of eminent interest to discover such forgery at an early point of time before large quantities of forged banknotes have been put into circulation, and it is also highly important to identify forgeries quickly and with certainty so that it is prevented that forged banknotes accidently are put into circulation again by the bank. Also it is of importance to use a method for checking or identification which is only available to well-trained scientists, thus considerably narrowing the circle of persons who would be able to carry out a serious effort to forgery.

Although the ESR technique is already known since the forties, up till now nobody has had the idea to use this technique for the identification of papers, particularly of valuable documents and banknotes and the like. The salts mentioned in Dutch patent application 6613250 per se would not be impossible to use for this purpose, but their identification with the aid of ESR is relatively difficult. Each compound of such a metal shows its own ESR spectrum, but its detectability suffers relatively much from accumelated dirt, and furthermore it is of course not detectable whether the concerning compound was already present in the unprinted paper or has been added in one or the colors of the printing ink. This again can lead to difficulties, when the pattern of the printing is changed (emission of banknotes, cheques or the like of a new model). Moreover, these salts are easily commercially available so that they do not essentially hamper forgery.

Among the compounds used in the other above-mentioned references dealing with fluorescence there may be some which show a suitable ESR spectrum, although to the knowledge of the present inventors this has never been investigated. However, a further requirement is that a useful ESR spectrum should be obtained at room temperature. Many compounds of rare earths and the like show a useful ESR spectrum only at low temperatures, such as the temperature of liquid nitrogen, but of course an identification of banknotes and the like is hardly of any practical value, if it cannot be carried out at normal room temperatures.

A primary object of the invention is to provide for a method of checking the authenticity of papers with the aid of ESR spectroscopy at room temperature.

A further object of the invention is to provide paper suitable for such a method.

A still further object is to provide such a method and paper, wherein the material which gives the characteristic ESR spectrum has been incorporated in a fiber woven in the paper.

Further objects and advantages of this invention will become clear from the following description.

According to the present invention a method has been found of checking the authenticity of papers in a physical way, comprising using authentic paper containing a minor amount of a substrate showing an ESR spectrum at room temperature, and checking the authenticity by ESR spectroscopy.

Also the invention provides a physically identifiable paper for use in the above method containing a minor amount of a compound of a metal which has an incompletely filled 3d or 4f orbital, wherein said compound shows an ESR spectrum at room temperature and is either an oxide or salt having a crystal lattice of cubic symmetry, doped with such a metal, or an oxide or salt of arbitrary symmetry of the crystal lattice doped with a freely rotatable ion containing such a metal.

Hereinafter the invention is further explained, also with the aid of the enclosed drawings.

Figure 5:
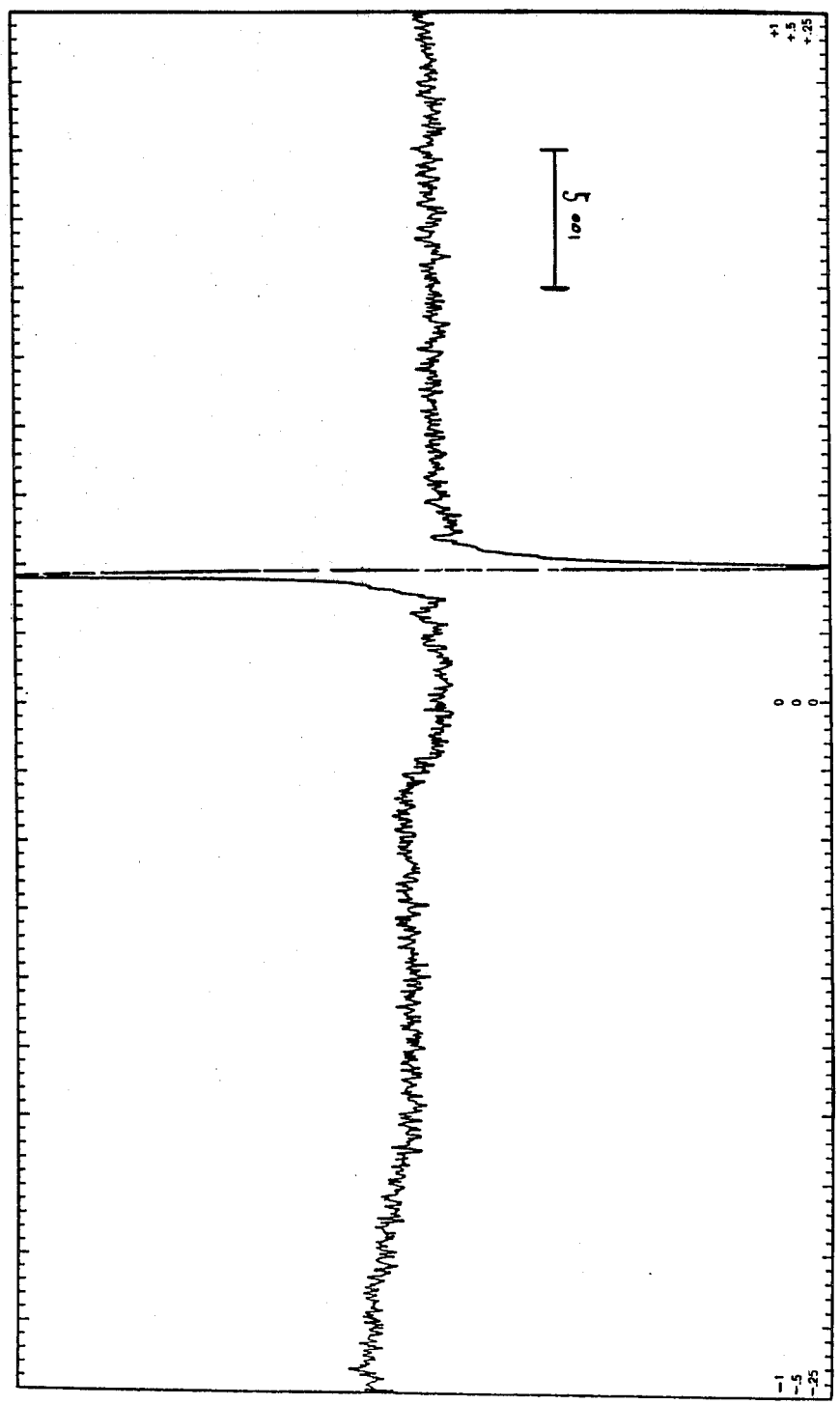
Figure 6:
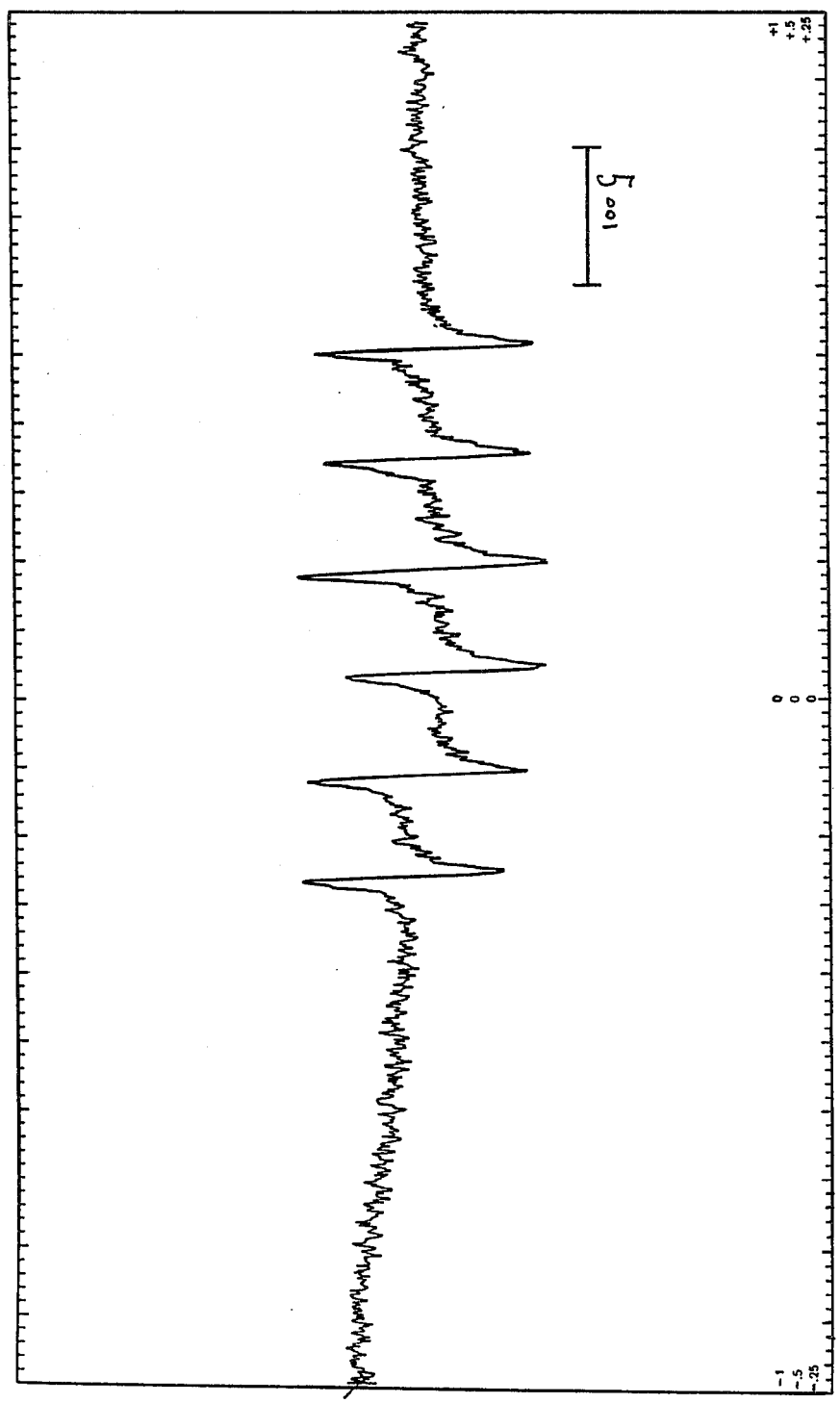

FIG. 5 shows the ESR spectrum of paper containing 3 weight % of $SrTiO_3$, doped with 1000 ppm of Cr; and FIG. 6 shows the ESR spectrum of paper impregnated with 3 weight % of $SrTiO_3$, doped with 1000 ppm of Mn, and 1 weight % of $SrTiO_3$, doped with 1000 ppm of Cr.

With the materials used according to this invention very clear ESR signals are obtained and this specifity is maintained, e.g. also in badly fouled banknotes. Due to the fact that compounds have been incorporated in the paper itself which normally do not occur in the printing inks, the compounds in the ink generally will not interfere with the signals of the additive. Consequently, the present invention opens the possibility to install an ESR device in main offices of large banks or at the central bank of a nation and so to detect quickly forgeries which otherwise would be detected much later or with much more difficulties. The first receiver of a forged banknote, a forged cheque or the like virtually never can be protected agaist a sophisticated forgery, but a soon discovery of a "good" forgery is of great importance for combatting the further distribution thereof.

According to the present invention two classes of materials enter into consideration. The first class is formed by oxides and salts having a crystal lattice of cubic symmetry, doped with the chosen metal or metals having a not completely filled 3d or 4f orbital. A particularly suitable doping metal is manganese with its half filled 3d orbital, as well as gadolinum having a half filled 4F orbital and normally not occurring in inks. In J. Phys. Soc. Japan 14 (1959), 108, ESR data for a great number of $Mn^{++}$ doped materials are found, measured at a wave length of 3 cm and at room temperature. Particularly suitable are doped materials having a value of the coupling constant, A, of more than $80,10^{-4}$ $cm^{-1}$. Other materials doped with $Mn^{++}$ and their A-values are as follows:

| Host | A, $10^{-4}{}_{cm}{}^{-1}$ |
|---|---|
| $K_2MgF_4$ | 91.5 |
| $NaMgF_3$ | 92.5 |
| $SrF_2$ | 95.2 |
| $CaF_2$ | 95.4 |
| $KCaF_3$ | 93.1 |

Particularly suitable materials are also some materials having a perovskite structure, for instance strontium titanate. Doped materials of this type have been disclosed in Dutch patent application No. 7604707, however as a ceramic material for an electric resistor.

Another class of particularly suitable host crystals is formed by the alkaline metal oxides, such as magnesia, calcia and strontia.

An extra safety measure in banknotes is the use of a thread or ribbon which is woven in the paper. This is for instance done in some British banknotes. According to an embodiment of the present invention the additive can be incorporated in the interior of such a filament or ribbon. This embodiment is particularly useful, if the host compound is water-soluble so that simple incorporation in the paper is not possible.

As mentioned already, the doping material can be any element having an incompletely filled 3d or 4f orbital and showing an ESR spectrum at room temperature. Also combinations of two or more of such elements can be used, which can lead to still more specific ESR spectra.

A second class of suitable materials is constituted by salts or oxides which are doped with a freely rotatable ion of an element having an incometely filled 3d or 4f orbital. In that case the host compound can possess any arbitrary symmetry of the crystal lattice. An example of such a freely rotatable ion is the vanadyl ion ($VO^{++}$). This can be incorporated for instance in potassium nitrate, cesium nitrate or ammonium chloride.

The incorporation of the chosen identification material in the paper can be carried out in any manner known per se and at any suitable point of time during the paper making process. Also the material can be incorporated only in the finished paper by impregnation and drying. In the case of a filament or ribbon containing the concerning material, these fibers of course are also incorporated in the paper in some known way. As mentioned already, the material present in these fibers can be water-soluble, but of course also water-insoluble materials can be used in this embodiment.

A further advantage is obtained by using materials of which the host crystal is a salt or oxide which is not further oxidizable. When documents, banknotes, cheques or the like, wherein such an identification material has been incorporated, are burnt, their authenticity still can be checked with the aid of the ash.

The following experiments will further elucidate the invention.

The measurements were performed with a Varian E4 X-band spectrometer in a $TE_{120}$ rectangular oscillation cavity. The ESR absorption derivative was detected with the aid of modulation coils on the outside cavity walls, operating at 100 kHz. The investigated samples were rolled up along the long side of the sheets and inserted into the cavity without any sample holder. In this instrument the sample contributed to the signal over a length of about 1 cm along the central cavity axis.

After a sample was put into the cavity, the loaded cavity was properly matched by means of an iris adjust screw, and the detector current was set to approximately the same value (200 $\mu A$) for each sample by varying the micro wave power.

Figure 1:
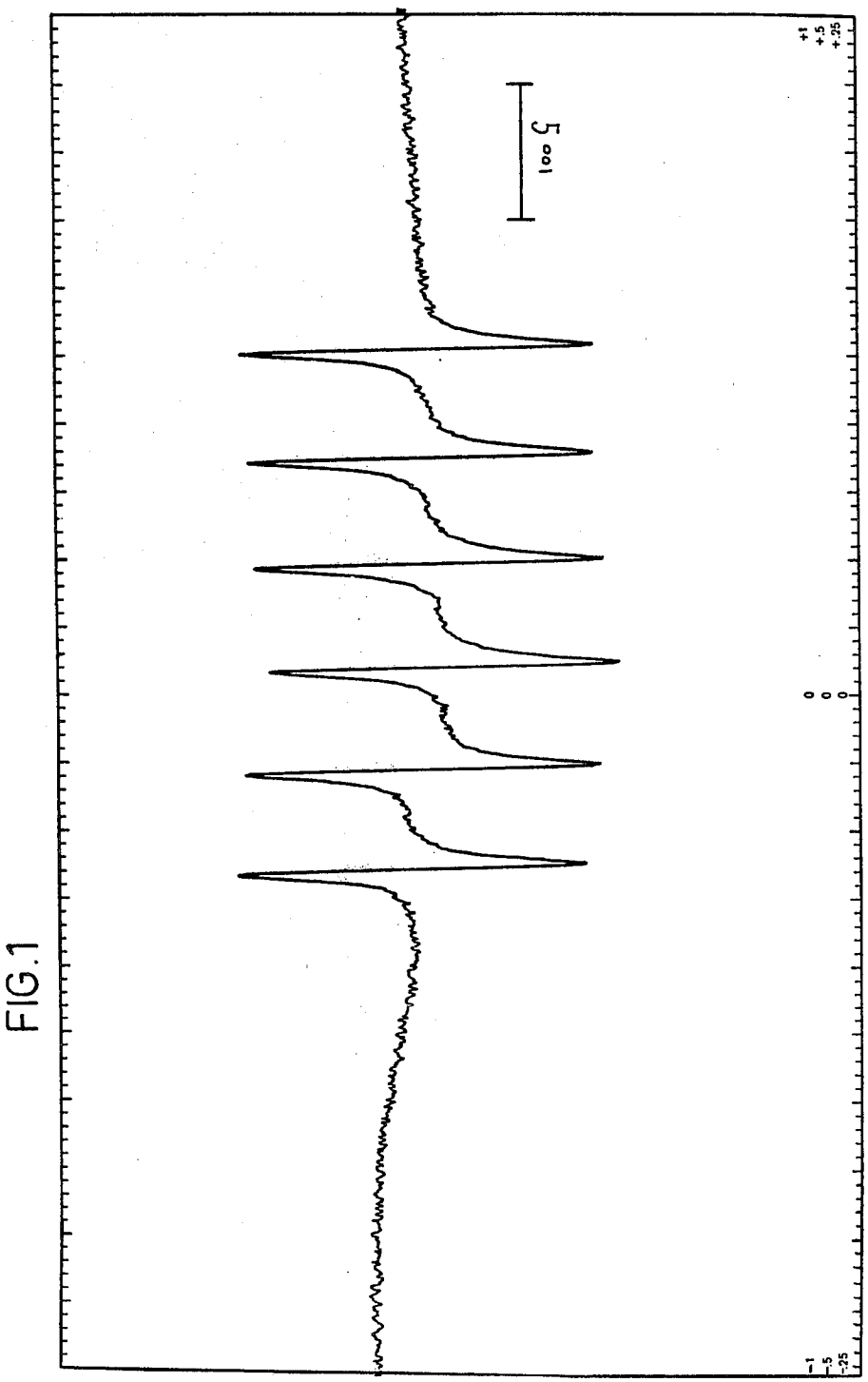
FIG. 1 is an ESR spectrum of paper containing 3 weight % of $SrTiO_3$, doped with 1000 ppm of Mn.

Test 1: In paper to be used for banknotes 3 weight % of $SrTiO_3$, doped with 1000 ppm of Mn, was incorporated. The ESR spectrum of the so treated paper has been rendered in FIG. 1. The spectrum shows the 6 peaks which are characteristic for manganese, but the distances between these peaks are in turn characteristic for the concerning compound. For identification purposes the distance between the two extreme peaks can best be used.

Figure 2:
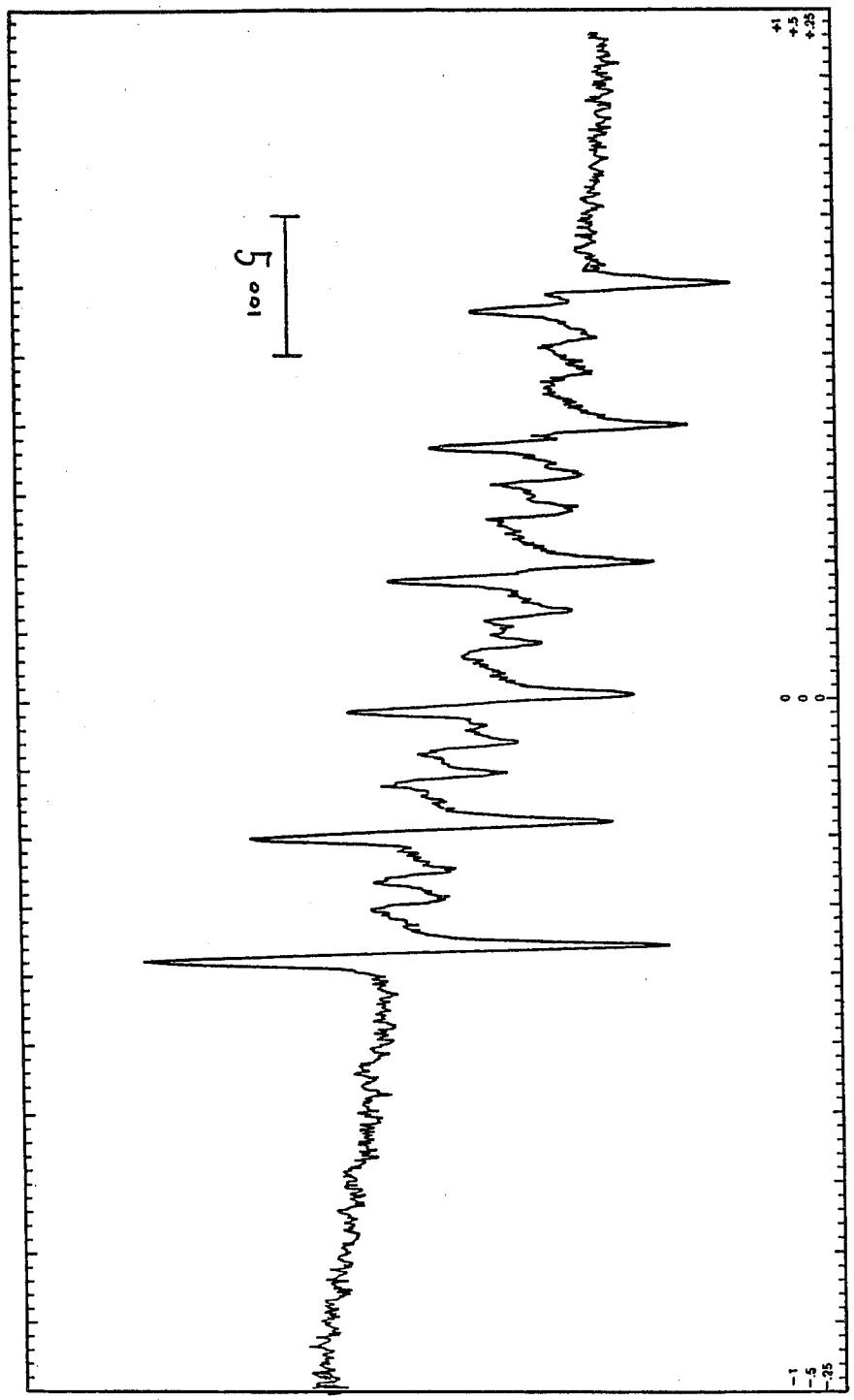
FIG. 2 shows the ESR spectrum of a relatively new banknote of Hfl. 25.

Test 2: The ESR spectrum of a relatively new banknote of Hfl. 25. was measured. This spectrum has been rendered in FIG. 2. Again one sees the 6 peaks which are characteristic for Mn, but the mutual distance is different from that in FIG. 1 and this appears particularly clearly from the distance between the two extreme peaks.

Figure 3:
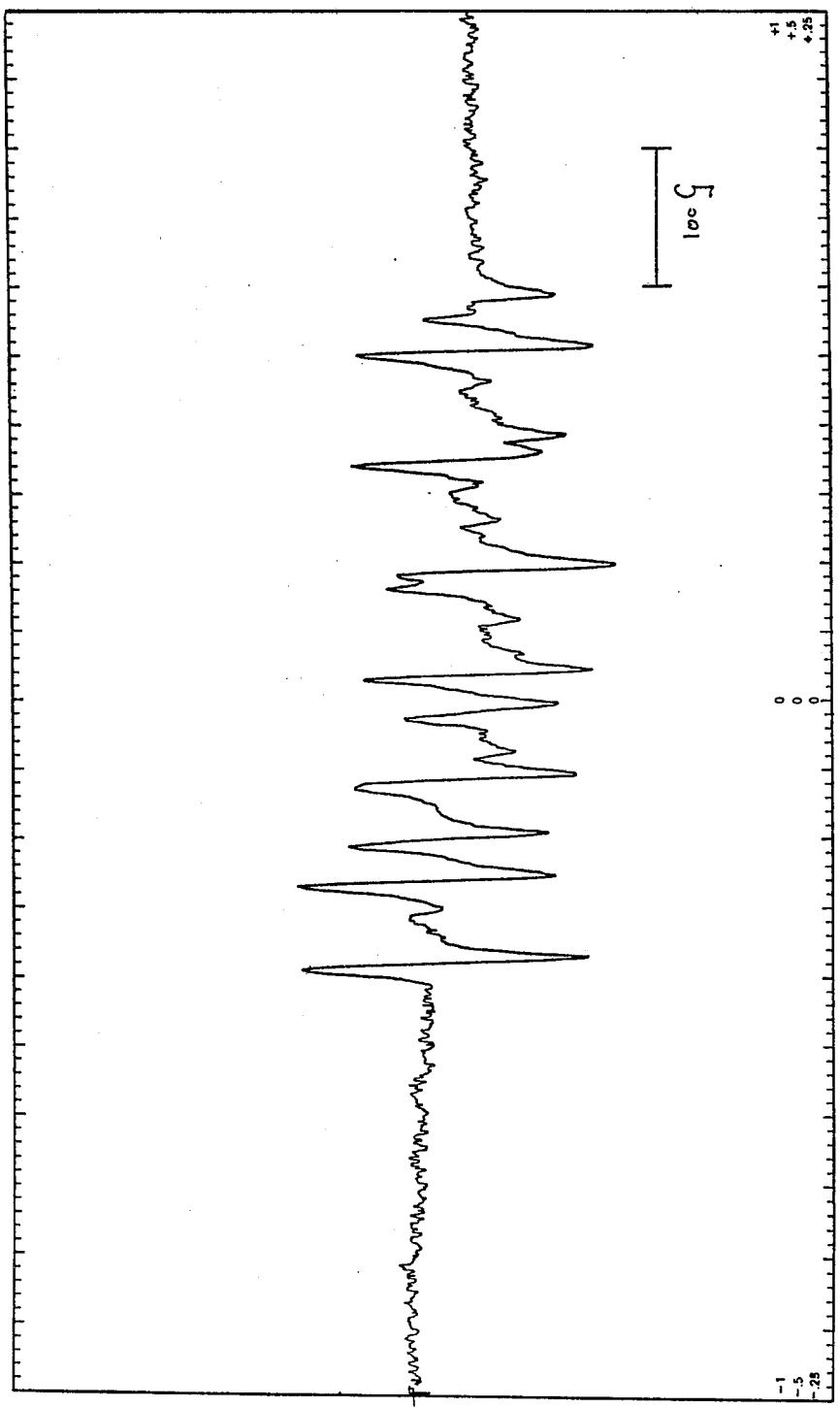
FIG. 3 shows the ESR spectrum of a combination of the paper of FIG. 1 and the banknote of FIG. 2.

Test 3: The paper of Test 1 and the banknote of Test 2 were superposed and the ESR spectrum of this combination was taken. The result is shown in FIG. 3. As was to be expected, a superposition is obtained. The distance between the two extreme peaks from FIG. 1 is found again here in FIG. 3. Of course this is also true for the different distance between the extreme peaks of FIG. 2, but it is immediately clear that the manganese compound in the printing ink is much less characteristic than the manganese-doped strontium titanate.

Figure 4:
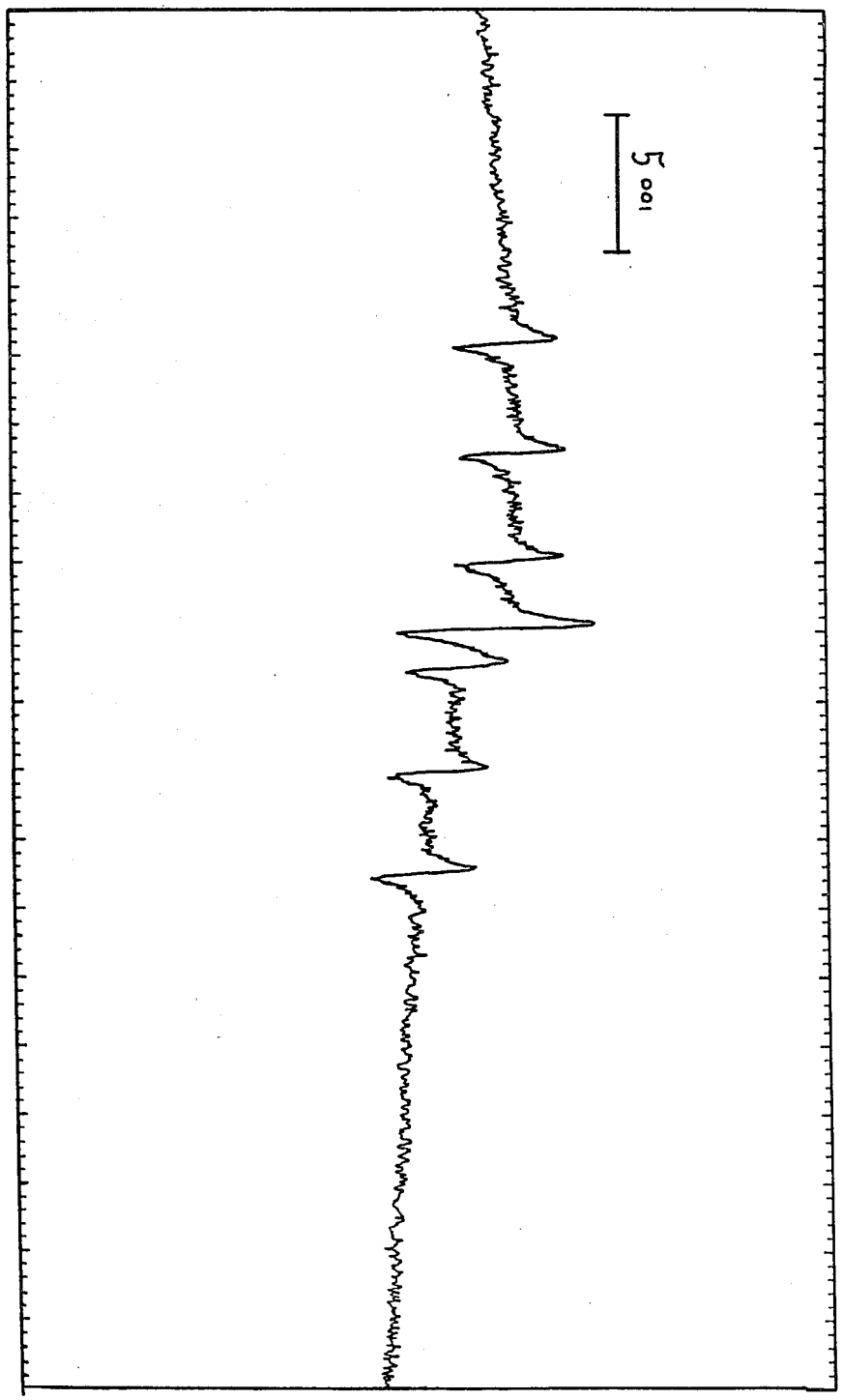
FIG. 4 shows the ESR spectrum of the ash obtained by burning the paper of FIG. 1.

Test 4: Paper as used in Test 1 was burnt and an ERS spectrum was taken from the ash. The result thereof is shown in FIG. 4. Of course, the general image of the spectrum is not identical to that of FIG. 1 (the additional peak presumably is caused by newly formed compounds), but the characteristic distance between the two extreme peaks of FIG. 1 again can be found back in this figure. Consequently, the doped strontium titanate is also suitable for the identification of burnt paper.

Test 5: In banknote paper again 3 weight % of $SrTiO_3$ was incorporated, which this time, however, had been doped with 1000 ppm of Cr. The ESR spectrum thereof has been rendered in FIG. 5. As appears therefrom, only one peak is obtained with chromium, which peak, however, is very strong. For identification purposes this material per se, appears less suitable than the material doped with manganese. However, it is a good combination component, as appears from the following test.

Test 6: Paper for banknotes was impregnated with 3 weight % of $SrTiO_3$ doped with 1000 ppm of Mn, as well as with 1 weight % of $SrTiO_3$ doped with 1000 ppm of Cr. The ESR spectrum of the so treated paper has been rendered in FIG. 6. Again one finds the same characteristic distance between the extreme peaks as in FIG. 1, but now the intensity ratio between the peaks has been modified in a way which is also characteristic.

What is clamed is:

1. A method of checking the authenticity of papers in a physical way which comprises using authentic paper containing a minor amount of a substance showing an electron spin resonance spectrum at room temperature, and checking the authenticity by electron spin resonance spectroscopy.

2. A method according to claim 1, wherein said paper is a banknote.

3. Physically identifiable paper for use in the method of claim 1 containing a minor amount of a compound of a metal which has an incompletely filled 3d or 4f orbital, characterized by the fact that said compound shows an electron spin resonance spectrum at room temperature and is either an oxide or salt having a crystal lattice of cubic symmetry doped with such a metal, or an oxide or salt of arbitrary symmetry of the crystal lattice doped with a freely rotatable ion containing such a metal.

4. Paper according to claim 3, wherein the doped salt or oxide has been incorporated in a fiber which has been woven in the paper.

5. Paper according to claim 3, wherein the doped material on burning of the paper constitutes a component of the ash.

6. Paper according to claim 3, wherein the oxide or salt has been doped with manganese.

7. Paper according to claim 3, wherein the oxide or salt has been doped with gadolinum.

8. Paper according to claim 3, wherein the host crystal has a perovskite structure.

9. Paper according to claim 3, wherein the host crystal is chosen from the group consisting of magnesia, calcia and strontia.

10. Paper according to claim 3, wherein the paper is a banknote.

* * * * *

UNITED STATES PATENT AND TRADEMARK OFFICE
CERTIFICATE OF CORRECTION

PATENT NO. : 4,376,264

DATED : March 8, 1983

INVENTOR(S) : Dokter et al

It is certified that error appears in the above-identified patent and that said Letters Patent is hereby corrected as shown below:

On the title page  Assignee should read:

-- [73] Assignee: Papierfabrieken Van Houtum & Palm B.V.,
           Ugchelen, Netherlands --.

Signed and Sealed this

Seventh Day of February 1984

[SEAL]

Attest:

GERALD J. MOSSINGHOFF

Attesting Officer    Commissioner of Patents and Trademarks